United States Patent [19]

Herold

[11] 4,298,806
[45] Nov. 3, 1981

[54] APPARATUS FOR IRRADIATING SUBSTANCES CURABLE BY RADIATION

[75] Inventor: Wolf-Dietrich Herold, Hechendorf, Fed. Rep. of Germany

[73] Assignee: ESPE Fabrik pharmazeutischer Praparate GmbH, Seefeld, Fed. Rep. of Germany

[21] Appl. No.: 1,590

[22] Filed: Jan. 8, 1979

[30] Foreign Application Priority Data

Jan. 23, 1978 [AT] Austria .................................. 451/78

[51] Int. Cl.³ .............................................. G01J 1/00
[52] U.S. Cl. ............................. 250/504 H; 250/472; 250/493
[58] Field of Search .................... 250/472, 504, 493 R

[56] References Cited

U.S. PATENT DOCUMENTS

| 1,800,277 | 4/1931 | Boerstler | 250/504 |
| 3,101,411 | 8/1963 | Richards | 250/504 |
| 3,712,984 | 1/1973 | Lienhard | 250/504 |
| 3,970,856 | 7/1976 | Mahaffey | 250/504 |
| 4,149,086 | 4/1979 | Nath | 250/504 |

Primary Examiner—Harold A. Dixon
Attorney, Agent, or Firm—Holman & Stern

[57] ABSTRACT

An apparatus for irradiating substances curable by radiation comprises a lamp the emitted radiation of which includes both the UVA or near-UVA spectral range required for the curing and spectral ranges outside these useful ranges. A glass substrate surrounding the lamp has an ellipsoidal concave surface carrying a thin-film filter which reflects only the useful radiation but transmits the undesired spectral ranges, particularly the major portion of the visible light and the thermal radiation. When the power consumption of the lamp decreases as a result of clustering of the filament, the power supply is periodically interrupted thereby producing a flashing signal to warn the user.

16 Claims, 4 Drawing Figures

APPARATUS FOR IRRADIATING SUBSTANCES CURABLE BY RADIATION

BACKGROUND OF THE INVENTION

An apparatus for irradiating substances curable by radiation of a selected spectral range is known from German Offenlegungsschrift No. 26 07 249. A lamp commonly used for movie projectors and including an aluminum reflector serves as the light source, and the entire radiation of the lamp which includes visible, ultraviolet and infrared spectral ranges, is focussed by the reflector to a focus situated in front of the lamp. A filter is disposed within the radiation cone between the reflector and the focus, which reflects the UVA spectral portion (320 to 400 nm) and transmits the remaining radiation. The filter is a thin filter layer deposited by evaporation onto a support plate of quartz glass extending at 45° with respect to the optical axis of the radiation cone. The portion of the radiation reflected by this filter is coupled into an optical wave guide and thereby directed onto the object to be irradiated.

The known apparatus is intended primarily for curing dental fillings of synthetic material polymerizable by ultraviolet radiation within the respective dental cavity. In this application, only the UVA-radiation is applied to the filling while both the longer-wave visible and thermal radiation and the unholesome shorter-wave radiation is filtered away. This undesired radiation transmits the filter and impinges on a thermal shield which is cooled by ventilation.

In the known apparatus, the deflection of the useful radiation from the optical axis of the radiation cone produced by the lamp is desired as it ensures that, even when this filter is damaged, no radiation of the undesired spectral ranges will be transmitted through the optical wave guide and thus to the object to be irradiated.

The known irradiation apparatus, however, has a number of severe disadvantages. The filter is exposed to a very high thermal load because it reflects only a small portion of the entire radiant power and because a portion of the remaining transmitted power is absorbed by the supporting plate of the filter. Furthermore, since the lamp is operated intermittently, the thermal load occurs as a changing load causing particular stress on the filter. Thus, the plane and thin filter glass plate, being in itself very fragile, forms a truly weak point of the known apparatus.

In order to make the apparatus as small and handy as possible and also to make the delicate filter plate as small as possible while simultaneously utilizing the full light cone produced by the lamp and the reflector, it is furthermore required to grind the filter at least partially oval, which causes difficulties in the manufacture due to the fragibility and is accordingly expensive.

For reasons resulting from the use of a commercially available light source having a standard reflector shape and again from the desire to make the entire apparatus as small and handy as possible, the space between the radiation cone produced by the light source and the input end of the optical wave guide is very limited so that it is difficult to mount additional filters between the first-mentioned filter and the optical wave guide without interfering with the light cone. Such additional filters may be necessary depending on the frequency characteristic of the thin-film filter.

A further and possibly the greatest problem of the known apparatus results from the fact that the filter characteristic of the thin-film filter used depends on the angle of incidence of the light beam. In case the thin-film filter is selected such that maximum reflection occurs at the average angle of incidence of 45° at a wave length of e.g. 350 nm, this maximum is moved towards smaller wave lengths with increasing angle of incidence and to greater wave lengths with smaller angles of incidence, as shown in the diagram of FIG. 3. Such greater and smaller angles of incidence, however, cannot be avoided with the geometry of the known apparatus. Indeed, a deviation of ±30° from the average angle of incidence of 45° must be taken into account. This causes a substantial shift of the filter characteristic for the peripheral portion of the radiation cone, resulting in less reflection of the desired spectral range and more reflection of the undesired and partly even harmful spectral range which latter must be absorbed by additional filters. It is furthermore to be considered that the near-axis rays which would be incident at the optimum angle of 45° occur not at all because of the evacuation nipple produced during manufacture at the tip of the lamp bulb and because of the absence of the central reflector portion where the lamp itself is mounted.

Moreover, in consideration of unavoidable tolerances in the mounting to the filter within the housing at the 45° position, a further deterioration of the filter function must be expected. Also, the mounting must take into account the above-mentioned thermal loads of the filter by allowing for an according play.

As a further disadvantage, the filter, the reflector and the input end of the optical wave guide together form a substantially closed chamber in which the heat produced by the light source will accumulate and put additional load on the reflection filter as well as any other absorption filters provided at the input of the optical wave guide.

In the field of movie and slide projectors, German Offenlegungschrift No. 1 572 759 and Austrian Pat. No. 215 180 disclose a reflector which substantially reflects only visible light and transmits thermal radiation. However, if such a reflector were used in an irradiation apparatus operating in the UVA range or near-UVA visible range for dental applications, at least one additional filter would be required to be disposed in the reflected radiation in order to separate this desired spectral range from the remaining, visible light. Using a reflection filter as such additional filter would result again in most of the above-discussed disadvantages.* If an absorption filter were used as the additional filter, there would be the further disadvantage that this filter is exposed to a particularly high thermal load and the risk of fracture resulting therefrom. Failure of this filter would entail the further disadvantage that the visible light would not be prevented from being transmitted by the optical wave guide to the object to be irradiated, where it will regularly interfere.

*particularly since a deflexion from the optical axis would be unavoidable.

It is an object of the invention to provide an apparatus for irradiating substances curable by radiation of a selected spectral range, which avoids at least part of the above-mentioned deficiencies and which, particularly, allows a more exact filtering, thus a better exploitation of the desired spectral range in the radiation produced by the light source. It is a further object to produce an apparatus of this type in which the thermal load on the various elements of the apparatus is reduced.

It is another object of the invention to provide an apparatus of the mentioned type with a structure which is inexpensive to manufacture and easy to handle.

As a further object of this invention, an irradition apparatus of the described type is to be achieved which provides an unambiguous warning to the user in case of malfunction of the radiation source.

SUMMARY OF THE INVENTION

The apparatus of the present invention for irradiating substances curable by radiation of a spectral range selected from the UVA and near-UVA visible wave length ranges comprises a lamp for emitting a radiation which includes said selected spectral range, a selective reflector which reflects radiation of said selected spectral range and transmits radiation outside thereof, said reflector partially surrounding said lamp so as to converge the reflected radiation to a focus situated outside said lamp on the side remote from said reflector, and an optical wave guide having an input end at said focus for directing said reflected radiation to said substances.

In this apparatus, the selective reflector performs the filtering of the light emitted by the lamp. This saves the additional filter element required by the known apparatus and avoids any mounting tolerances. In the apparatus of this invention, the undesired radiation is immediately transmitted by the reflector whereby the heat may be removed without difficulty by according cooling means. Only cold radiation in the predetermined desired spectral range is radiated from the front of the reflector so that any absorption filter that may be required and the optical wave guide itself are exposed to no thermal load. If the reflector is shaped as part of an ellipsoide of revolution, the angle of incidence of the radiation varies only slightly across the filter surface so that a well defined filter characteristic is achieved and even the periphery of the radiation cone carries practically no undesired or even harmful spectral portions.

According to an advantageous development of the invention, the input end of the optical wave guide extends coaxially with the axis defined by the lamp and the said focus. This not only results in a particularly handy apparatus but also avoids constructional limitations on the mounting of any additional filters that may be required in front of the optical wave guide. In spite of this coaxial arrangement of the wave guide with respect to the optical axis of the lamp, there is no risk of unfiltered light arriving at the object to be irradiated in case of damage of the reflector because the direct, unreflected radiation of the lamp is largely scattered by the above-mentioned evacuation nipple at the tip of the lamp bulb. The coaxial disposition of the optical wave guide and the radiation source further permits providing a handle on the apparatus in a position which is best suited for the handling of the apparatus. An inclination of the handle with respect to the optical axis of the lamp at an angle of about 80° has proven particularly convenient.

In another useful development of the invention, the apparatus comprises monitor means for periodically interrupting the power supplied to the lamp when the power consumption of the lamp decreases. Such decrease of the irradiation power, which occurs when the filament becomes clustered and which cannot be recognized from the radiation emitted by the optical wave guide, is indicated by a flashing signal providing the user with a clear warning as to the malfunction of the lamp.

DETAILED DESCRIPTION OF A PREFERRED EMBODIMENT

Figure 1:
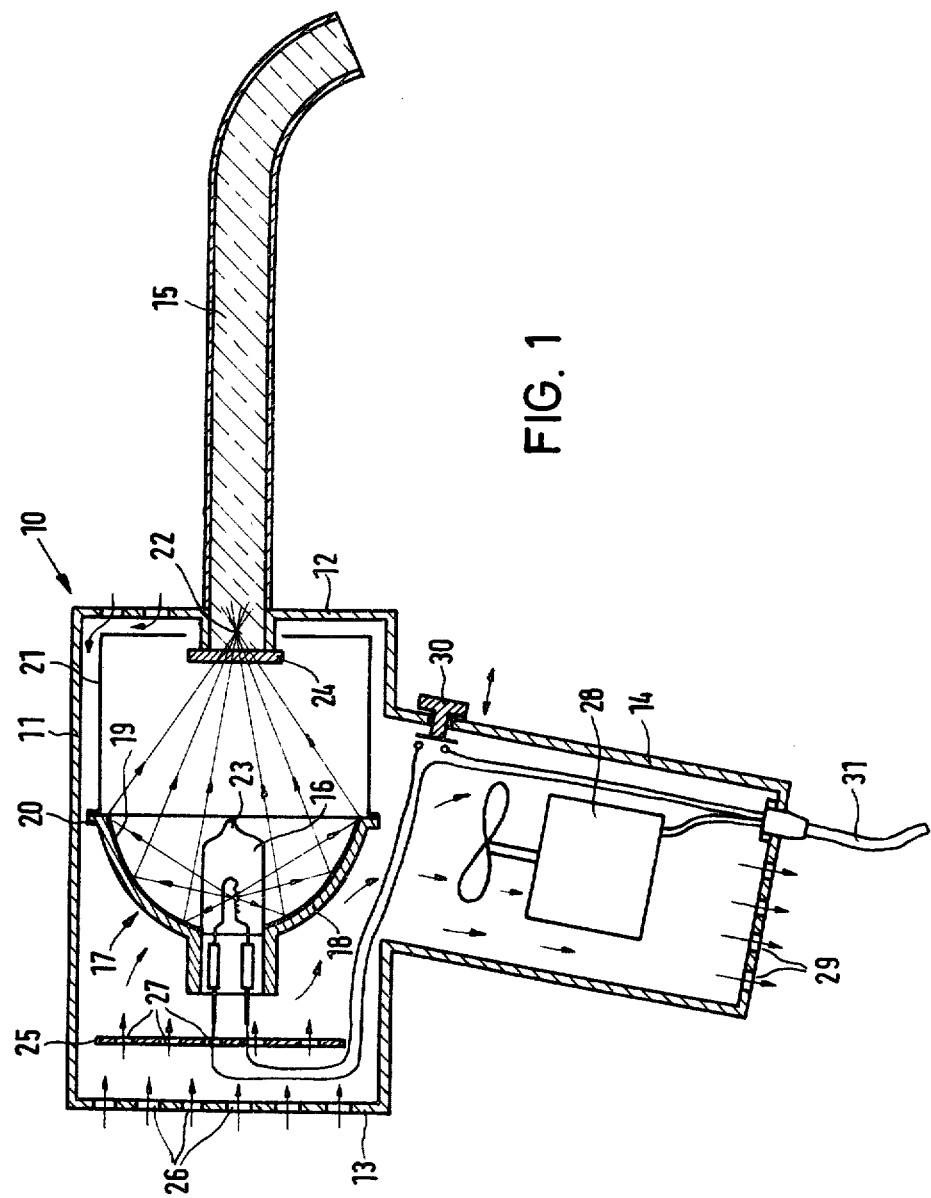
FIG. 1 is a diagrammatic longitudinal section through an irradiation apparatus.

The irradiation apparatus shown in FIG. 1 includes a housing 10 of e.g. plastics material having a shell 11 which may be cylindrical, a front wall 12 and a rear wall 13. A handle 14 is formed on the shell 11 which handle may also be cylindrical, the axis of the handle 14 extending at a convenient angle of e.g. about 80° with respect to the axis of the housing 10. A rigid optical wave guide 15 extends through the front wall 12 of the housing 10, the input end of the wave guide 15 projecting into the interior, and the output end of the wave guide being bent.

A lamp 16 cemented in a reflector 17 is mounted inside the housing 10 along the axis of the housing. The reflector 17 includes a substrate 18 of industrial glass suited for rapidly changing temperatures, particularly borosilicate glass, having an ellipsoidal inner surface provided with a thin-film filter 19. According to its reflection-transmission characteristic, the reflector functions as a "selective reflector". The thin-film filter 19 may be formed by vapor deposition of multiple $TiO_2$ layers having a refraction index of about 2.4. A flange 20 provided on the periphery of the reflector substrate 18 is mounted inside the housing 10 by means of a bracket 21.

The lamp 16 may be a commercially available low-voltage lamp including a tungsten filament and a halogen filling and is supplied with an elevated voltage for producing a sufficient proportion of short-wave radiation. Alternatively, other types of lamps such as gas discharge lamps may be used as long as the emitted radiation comprises the desired spectral range. Similarly as the lamp 16, the reflector substrate 18 may be a conventional element. The various optical parts of the apparatus are so disposed that the filament of the lamp 16 is in one focus of the ellipsoide of revolution formed by the reflector surface while its other focus 22 is inside the optical wave guide 15 near the input end thereof. Both foci define the optical axis of the reflector 17 which coincides with the optical axis of the optical wave guide 15 and that of the housing 10.

The thin-film filter 19 is selected such that it preferably reflects the desired spectral portion of the radiation emitted by the lamp 16 and transmits the remaining spectral portions. Since the apparatus is intended primarily for use in polymerizing dental fillings of synthetic material inserted into dental cavities, the thin-film filter 19 is so adjusted that its reflection maximum is in the UVA range (approximately 320 to 400 nm) and/or in the near-UVA visible spectral range (approximately 400 to 500 nm). Due to the shape and disposition of the filament within the lamp 16, the major portion of the radiation is emitted in directions deviating from the optical axis and impinges on the reflector 17 thereby being filtered. The small portion of the radiation emitted forwardly along the optical axis is scattered by the evacuation nipple 23 caused by the manufacture at the tip of the lamp bulb so that practically no radiation is transmitted directly to the optical wave guide 15 without being filtered. An absorption filter 24 is disposed at the input end of the optical wave guide 15 for further filtering away undesired spectral ranges.

The radiation transmitted by the thin-film filter 19, a large portion of which is thermal radiation, impinges on a heat conducting element 25 disposed behind the reflector 17 for protecting the plastics housing 10 against excessive heating and simultaneously preventing radiation from emerging through ventilation holes 26 provided in the rear wall 13 of the housing 10. For increasing air circulation, the heat conducting element 25 also is provided with ventilation holes 27 which are offset from the ventilation holes 26.

The interior space of the hollow handle 14 communicates with the interior space of the housing 10. A fan 28 is accomodated in the handle 14 for removing the heat generated at the rear side of the reflector 17. The fan 28 draws fresh air through the ventilation holes 26 and 27 against the heat conducting element 25 and the rear side of the reflector 17 and expels the heated air through ventilation holes 29 provided at the lower end of the handle 14 to the atmosphere.

A switch 30 actuable by the thumb or forefinger for switching on the lamp 16 is provided in the handle 14. Power for the lamp 16 and the fan 28 is supplied via a cable 31 extending from the lower end of the handle 14 and connected to a control unit. A portion of the circuitry of this control unit is shown in FIG. 4.

Figure 2:
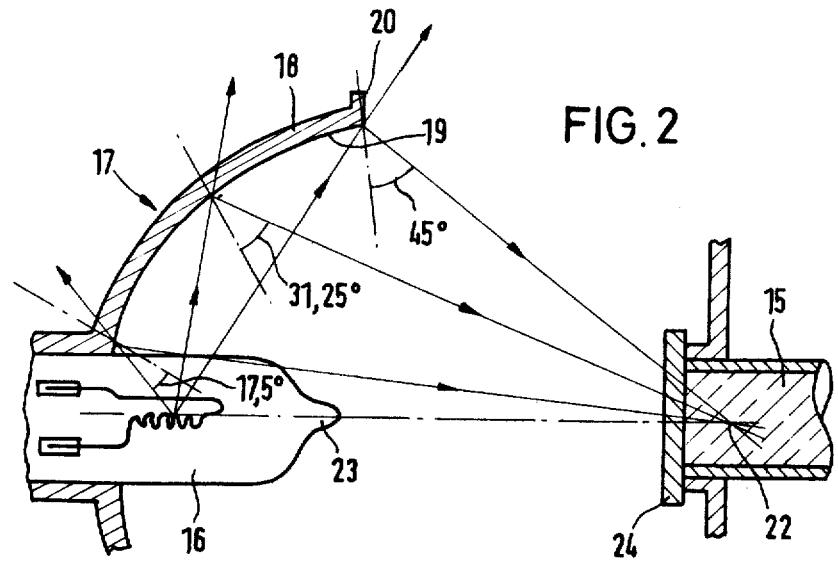
FIG. 2 shows certain details of FIG. 1 on an enlarged scale for explaining various ray paths.
Figure 3:
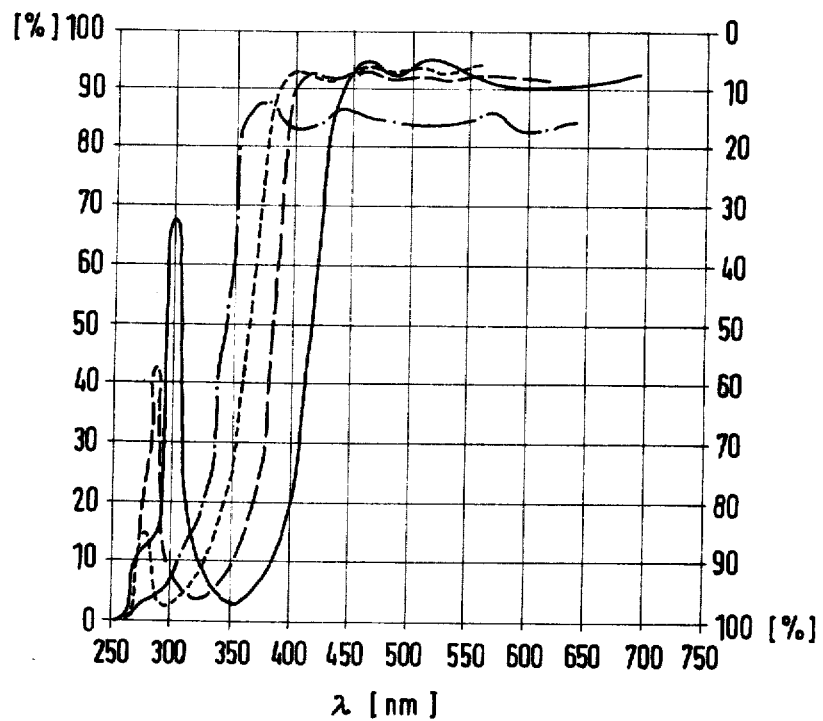
FIG. 3 which has been referred to above, shows a graph in which a number of characteristics of a thin-film filter are depicted with the angle of incidence as the parameter.

As will be understood from the enlarged detailed representation of FIG. 2, the angle of incidence of the light rays emitted by the lamp 16 varies across the profile of the reflector 17 between about 17.5° at the innermost reflector portion adjacent the lamp 16 and about 45° at the periphery of the reflector. If the thin-film filter 19 is adjusted such that the reflection maximum at an angle of incidence of 31.25°, i.e. at the arithmetical mean value of the two limit angles, falls in the desired spectral range, the comparatively small deviations of the angle of incidence of ±13.75° result in an accordingly small broadening of the filter characteristic, which is easily verified by reference to the graph of FIG. 3.

Figure 4:
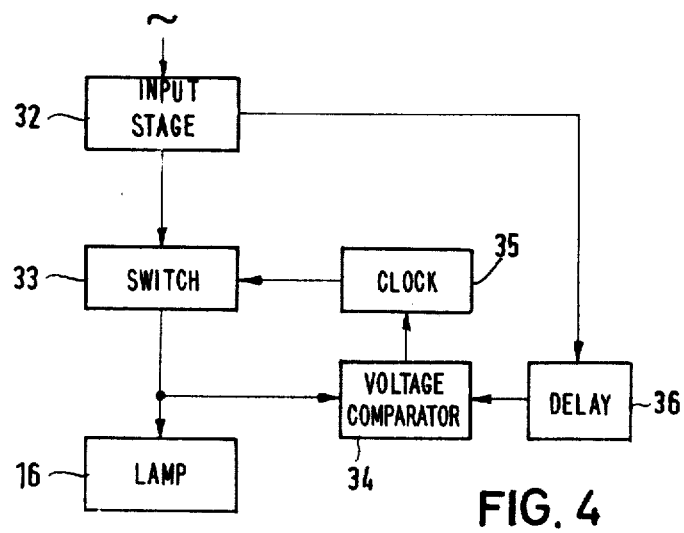
FIG. 4 is a block diagram showing a portion of a control unit for the apparatus shown in FIG. 1.

In accordance with the block diagram shown in FIG. 4, the lamp 16 is powered from the mains by a circuit which includes an input stage 32 and a controlled switching device 33 connected between the input stage 32 and the lamp 16. The power supplied by the mains is transformed by the input stage 32 such that in constant-current operation a voltage drop of 13 V normally occurs across the lamp 16. A voltage comparator 34 compares the lamp voltage with a predetermined value of e.g. 11.5 V. If the lamp voltage falls below this value, which may occur particularly upon extended use of the lamp as a result of the tungsten filament becoming clustered and thus shortened, the voltage comparator 34 actuates a clock pulse generator 35 which in turn controls the switching device 33 periodically at an interval of e.g. 1 s. This periodically interrupts the beam of light emerging from the output end of the optical wave guide, which provides the user with a conspicuous flashing signal clearly indicating that the lamp operates no longer properly and requires replacing.

A radiation power reduced by only a certain portion due to a partial short-circuit of the filament could not be recognized without this flashing signal, although such reduced radiation power would be insufficient for properly curing the irradiated material.

Because the lamp voltage rises not abruptly but within a time interval of about 0.8 to 4 s upon switching on the lamp, the voltage comparator 34 is enabled by a delay circuit 36 which is actuated by the input stage 32 upon switching on the lamp, and which has a delay time of 2 to 4 s.

I claim:

1. An apparatus for irradiating substances curable by radiation of a spectral range selected from the UVA and near-UVA visible wave length ranges, comprising
   (a) a lamp for emitting a radiation including said selected spectral range;
   (b) a selective reflector which reflects radiation of said selected spectral range and transmits radiation outside thereof, the reflector partially surrounding said lamp so as to converge the reflected radiation to a focus located outside said lamp at the side remote from said reflector; and
   (c) an optical wave guide having an input end at said focus for guiding said reflected radiation to said substances.

2. The apparatus of claim 1, wherein said selective reflector includes a substrate of transparent material and a thin-film filter deposited on a surface of said substrate.

3. The apparatus of claim 2, wherein said substrate consists of heat-resistant glass.

4. The apparatus of claim 2, wherein the surface of said substrate carrying said thin-film filter is shaped as part of an ellipsoide of revolution.

5. The apparatus of claim 1, wherein said input end of said optical wave guide extends coaxially with the axis defined by said lamp and said focus.

6. The apparatus of claim 5, further comprising
   (d) a housing carrying said lamp, selective reflector and optical wave guide; and
   (e) an elongate handle mounted on said housing so as to extend at an angle of about 80° with respect to said axis.

7. The apparatus of claim 6, further comprising a fan mounted in an interior hollow space of said handle, said housing including a space disposed at the rear side of said reflector and communicating with said interior space of said handle.

8. The apparatus of claim 7, comprising heat conducting means disposed in said space behind said reflector and simultaneously forming light shielding means.

9. The apparatus of claim 1, wherein said lamp is a low-voltage tungsten-halogen lamp.

10. The apparatus of claim 1 comprising additional filter means disposed at said optical wave guide input end.

11. The apparatus of claim 1, comprising means for supplying power to said lamp, and monitor means for periodically interrupting said power supply means when the power consumption of said lamp decreases.

12. An apparatus for irradiating substances curable by radiation of a spectral range selected from the UVA and near-UVA visible wave length ranges, comprising:
   (a) a lamp for emitting a radiation including said selected 5 spectral range;

(b) a selective reflector which reflects radiation of said selected spectral range and transmits radiation outside thereof, the reflector partially surrounding said lamp so as to converge the reflected radiation to a focus located outside said lamp at the side remote from said reflector;

(c) an optical wave guide having an input end at said focus for guiding said reflected radiation to said substances;

means for supplying power to said lamp; and monitor means for periodically interrupting said power supply means when the power consumption of said lamp decreases;

wherein said power supply means operates in a constant-current mode, said monitor means including means for comparing the voltage of said lamp with a threshold value, clock pulse generating means actuated by an output signal of said comparing means, and switching means provided in said power supply means and controlled by said clock pulses.

13. The apparatus of claim 12, comprising delay means for enabling said monitor means upon expiry of a time interval upon switching on said power supply means.

14. An apparatus for irradiating substances curable by radiation of a spectral range selected from the UVA and near-UVA visible wave length ranges, comprising
(a) a lamp for emitting said radiation;
(b) means for supplying power to said lamp; and
(c) monitor means for periodically interrupting said power means when the power consumption of said lamp decreases.

15. An apparatus for irradiating substances curable by radiation of a spectral range selected from the UVA and near-UVA visible wave length ranges, comprising:
(a) a lamp for emitting said radiation;
(b) means for supplying power to said lamp; and
(c) monitor means for periodically interrupting said power means when the power consumption of said lamp decreases;

wherein said power supply means operates in a constant-current mode, said monitor means including means for comparing the voltage of said lamp with a threshold value, clock pulse generating means actuated by an output signal of said comparing means, and switching means provided in said power supply means and controlled by said clock pulses.

16. The apparatus of claim 15, comprising delay means for enabling said monitor means upon expiry of a time interval upon switching on said power supply means.

* * * * *